United States Patent
Herrmann

[19]

[11] Patent Number: 5,977,780
[45] Date of Patent: Nov. 2, 1999

[54] MOISTURE AND DENSITY SENSOR

[75] Inventor: Rainer Herrmann, Hamburg, Germany

[73] Assignee: Manfred Tews, Hamburg, Germany

[21] Appl. No.: 09/104,124

[22] Filed: Jun. 24, 1998

[30] Foreign Application Priority Data

Jul. 2, 1997 [DE] Germany ................ 297 11 571 U

[51] Int. Cl.⁶ ............... G01N 9/00; G01R 27/04; H01P 7/10
[52] U.S. Cl. ................. 324/640; 324/634; 324/636; 73/29.05; 73/32 R; 333/219.1
[58] Field of Search ............... 73/32 R, 335.04, 73/29.05; 324/663, 640, 639, 664, 634, 636; 131/668, 906; 333/219.1

[56] References Cited

U.S. PATENT DOCUMENTS

| | | | |
|---|---|---|---|
| 3,694,737 | 9/1972 | Busker et al. | 324/636 |
| 4,131,845 | 12/1978 | Pakulis | 324/640 |
| 4,155,035 | 5/1979 | Fitzky | 324/58.5 C |
| 4,297,874 | 11/1981 | Sasaki | 73/73 |
| 4,326,542 | 4/1982 | Laszlo et al. | 131/906 |
| 4,477,771 | 10/1984 | Nagy et al. | 324/636 |
| 4,600,879 | 7/1986 | Scully et al. | 324/640 |
| 4,755,743 | 7/1988 | Jakkula | 324/640 |
| 4,890,054 | 12/1989 | Maeno et al. | 324/58.5 A |
| 5,105,158 | 4/1992 | Fiedziuszko et al. | 324/693 |
| 5,397,993 | 3/1995 | Tews et al. | 324/634 |
| 5,455,516 | 10/1995 | Jean et al. | 324/636 |
| 5,585,732 | 12/1996 | Steele et al. | 324/663 |
| 5,698,986 | 12/1997 | Mays et al. | 324/636 |
| 5,736,864 | 4/1998 | Moller | 324/634 |
| 5,764,116 | 6/1998 | Ishikawa et al. | 333/219.1 |

FOREIGN PATENT DOCUMENTS 0 789 237 A1  8/1997  European Pat. Off. .

*Primary Examiner*—Hezron E. Williams
*Assistant Examiner*—Chad Soliz
*Attorney, Agent, or Firm*—Alix, Yale & Ristas, LLP

[57] ABSTRACT

A microwave resonator for connection to an instrument for measuring the density and/or moisture profile in the longitudinal direction of a sample, which microwave resonator has a through-hole (3) at right angles to its area extent, which through-hole (3) is bounded by metallic walls (4) extending in the longitudinal direction, distinguishes itself in that the interior (1) of the resonator is essentially flat, with a thickness which is considerably less than the lateral dimensions at right angles to it, and in that the resonator is filled with a dielectric.

8 Claims, 8 Drawing Sheets

MOISTURE AND DENSITY SENSOR

FIELD OF THE INVENTION

The invention relates to a microwave resonator for connection to an instrument for measuring the density and/or moisture profile in the longitudinal direction of a sample. The invention also relates to an instrument for such measurements.

BACKGROUND OF THE INVENTION

It is often necessary to measure the density and/or moisture profile in the longitudinal direction of a sample. Important examples of this are the density measurement in a cigarette production line, the density measurement or moisture measurement in a woolen fibre, a plastic profile or other elongated materials. However, such measurements also have to be carried out with relatively short samples. If one wishes to determine the density and/or moisture profile in a wood-fibre board or chipboard, then a cylindrical core is often drilled out, along whose cylinder axis the density or moisture profile is then recorded.

Various methods are known for such measurements of density and moisture profiles.

Cigarettes are produced in large quantities by cigarette machines (up to 15,000 cigarettes per minute). It is necessary to measure the density exactly in order, in the process, to obtain optimum tobacco compression at one or both cigarette ends. Nowadays, this is carried out as a rule using gamma rays. The damping of the highly energetic photons is in this case dependent not only on the density but also on the composition of the material to be measured, and, in particular, on the water content of the tobacco as well. Density measurement is thus subject to uncertainties. Furthermore, efforts are, of course, being made to avoid the dangerous gamma radiation measurement technique. The use of infrared radiation for such measurements has the disadvantage of severe sensitivity to surface effects. It is thus not possible to achieve absolute density values, but only percentage statements relative to a maximum value for one tobacco type.

Density profile measurement in the case of wood-fibre boards is also an important process parameter in terms of quality assurance. The most important measurement method to date is also the gamma radiation method developed in the mid-1970s. Once again, it is disadvantageous here that the sensitivity to product moisture also limits the measurement accuracy of the density measurement.

It is known for both the density and the moisture of materials to be measured using microwaves, the products to be investigated being inserted into a microwave resonator (EP 0 468 023 B1). However, the disadvantage of this already known method is that the resonators and samples must be relatively large, so that it is not possible to measure a density or moisture profile with millimetric resolution. The reason for this is that the microwave frequency cannot be increased indefinitely since, otherwise, it would no longer be possible to obtain accurate readings. The measurements should thus be carried out with microwaves in a frequency band from 0.5 GHz up to a maximum of 15 GHz, which corresponds to wavelengths of 60 cm to 2 cm. One particularly useful frequency in this case is 2.5 GHz, which corresponds to a wavelength of 12 cm. In this case, the dimensions of the microwave resonators are normally in the same order of magnitude as one wavelength.

A microwave resonator of the type mentioned initially is known which has internally a projection through which the material to be measured moves (EP 0 292 571 claim 1). This microwave resonator also makes it possible to carry out measurements at a relatively low frequency. The actual measurement range is in this case relatively small owing to the short distance between the projection end and the opposite cavity wall. However, the field is highly inhomogeneous. The microwave field is very strong in the center and decreases considerably toward the edge so that, on the one hand, it is impossible to carry out a uniform measurement over the entire sample and, on the other hand, fluctuations occur in the readings if the sample is also moving in the transverse direction.

SUMMARY OF THE INVENTION

The object of the invention is to provide a microwave resonator as well as an instrument with such a microwave resonator, by means of which density and moisture measurements can be carried out with high accuracy and resolutions.

The solution according to the invention comprises the interior of the resonator being essentially flat, with a thickness which is considerably less than the lateral dimensions at right angles to it, and the resonator being filled with a dielectric.

The combination of a very flat microwave resonator and the dielectric filling in it results in a highly homogeneous microwave field in the actual measurement range, as a result of which accurate measurements can be carried out over the entire cross section of the sample, inaccurate alignment of the sample in the transverse direction having only a very small influence on the measurement result.

It is admittedly known for a microwave resonator to be produced from a dielectric (U.S. Pat. No. 5,105,158 A), which, however, intrinsically forms a microwave resonator without having to be enclosed by a metallic conductor which forms the actual microwave cavity, as in the case of the subject matter of the application. This resonator composed of a dielectric is also not used to carry out measurements in the longitudinal direction of a sample. Instead, measurements there are intended to be carried out on laminar samples. Owing to these differences, the field configuration is completely different, so that no stimuli toward the microwave resonator as set forth in this invention can be taken from the citation.

Astoundingly, the microwave resonator can be made very flat, its thickness being considerably less than the wavelength of the microwaves. Adequate field strengths are nevertheless obtained in the vicinity of the sample so that moisture and density can be measured in a small volume element by shifting the resonance curve as well as its spread in the manner known per se (EP 0 468 023 B1), so that it is possible to record the density and/or moisture profile in the longitudinal direction of the sample. The range of readings can be limited to 1 to 3 mm, the shorter lengths being used, for example, for cigarettes, and the greater lengths for wood-fibre samples. The metallic walls prevent the microwaves from propagating into free space.

If, as set forth in an advantageous embodiment, the resonator is filled with a dielectric, which completely fills the resonator with the exception of the opening for the sample to pass through, the resonant frequency is increased or, if the frequency is constant, the dimensions of the cavity are reduced. The measurements can in this case be carried out with low-power microwaves (less than 10 milliwatts), so that no significant heating of the sample takes place.

The thickness of the resonator is advantageously at least approximately 5 times less than its lateral dimensions, and, in particular, is at least approximately 10 times less. The chosen dielectric is advantageously one which has a relative dielectric constant ε of 2 to 100, advantageously of 7 to 15.

If the through-holes are lengthened outward by metallic tubes, this prevents microwaves from being able to propagate outward through the through-holes, in addition to the walls of the through-hole, which would make the resonance behavior poorer and would make the measurement less accurate, or even impossible.

A cylindrical resonator which is operated in the $E_{n10}$ mode (n=0, 1, 2) has been found to be particularly advantageous. Another advantageous embodiment is distinguished by the resonator being rectangular and being operated in the $E_{110}$, $E_{120}$ or $E_{220}$ mode.

BRIEF DESCRIPTION OF THE DRAWINGS

The invention is described in the following text using advantageous embodiments and with reference, by way of example, to the attached drawings, in which:

FIG. 5b shows the intensity of the electrical field strength in the lateral direction in the case of the embodiment in FIG. 5a;

FIG. 6b shows the electrical field strength in the lateral direction in the case of the embodiment in FIG. 6a;

DETAILED DESCRIPTION OF THE INVENTION

Figure 1:
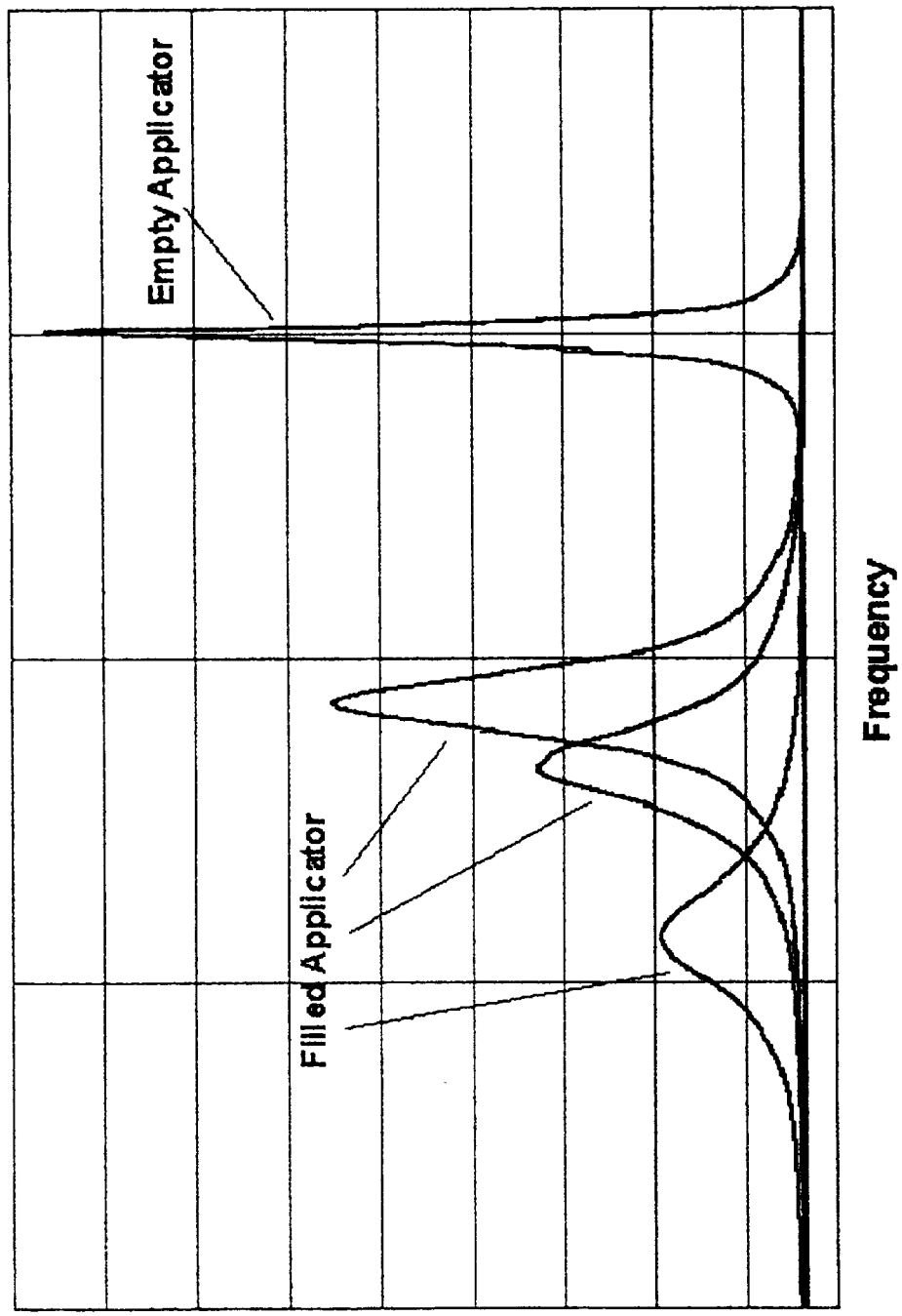
FIG. 1 shows a microwave resonance curve of a resonator in the state without a sample (empty resonator) or with a sample (filled resonator)

FIG. 1 shows the resonance curves of a resonator. It can be seen that the resonant frequency moves to lower frequencies as the filling level of the resonator rises, the amplitude of the resonance curves decreasing, and the width increasing, at the same time. This allows the density and the moisure to be determined using the known method.

Figure 2:
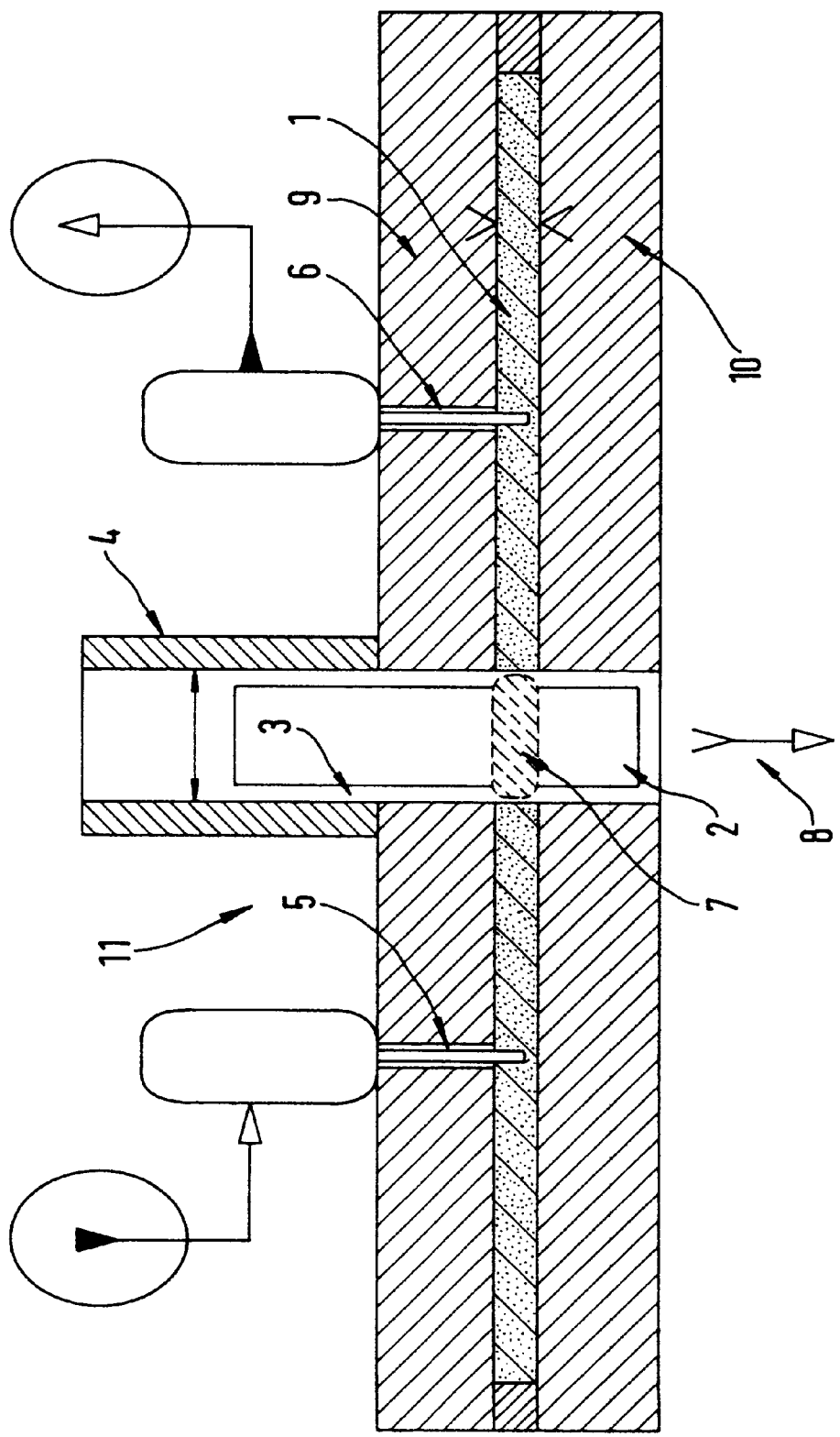
FIG. 2 shows a cross section of an embodiment of a cylindrical resonator while a cigarette is being measured.

FIG. 2 shows a cross section through a circular cylindrical microwave resonator 11 as claimed in the invention, which is bounded by an upper metallic wall 9 and a lower metallic wall 10 and is filled with ceramic material 1. This is used for measuring a wood sample 2, which moves through the resonator 11 in the direction of the arrow 8. The design of the corresponding microwave resonator for cigarettes is in this case in principle the same, only its dimensions being smaller. In particular, there, the passage for the sample does not have a diameter of 35 mm, but a considerably smaller diameter, which is only insignificantly larger than the cigarette diameter, that is to say approximately 9 to 10 mm. The sample 2 is moved through a through-hole 3, to the outside of which a short metal tube 4 is also fitted, which is intended to prevent microwaves from emerging. The microwaves are injected via an antenna 5 and are output via a further antenna 6. Instead of the transmission measurement, it is, of course, also possible to use a reflection measurement with only one antenna. The active measurement zone, whose thickness is approximately the same as that of the ceramic material 1, is denoted by 7.

The specific focusing onto a three-dimensional area of a few millimeters (down to 1–3 mm) is achieved by exciting the resonators in specific circular cylindrical E-resonance modes (transverse H modes, that is to say modes which have only one electrical field in the direction of the resonator axis), whose longitudinal mode number is zero, this being equivalent to the requirement of the electrical field lines to run by the shortest possible route between the metallic bottom plate and the top plate. The modes of practical importance for cigarette measurement are the $E_{010}$ resonance mode (fundamental mode of the circular cylindrical resonator) as well as, for wood-fibre board measurement, the $E_{110}$ and $E_{210}$ modes (1st number: azimutal symmetry description for rotation about the longitudinal axis, 2nd number: radial symmetry description=number of nodes in the radial direction, 3rd number: longitudinal symmetry description).

Rectangular resonators can also be used for profile measurement by using the rectangular $E_{110}$ mode instead of the $E_{010}$ mode in the fundamental mode in such a manner that the flattening for focusing is carried out such that the electrical field lines run by the shortest possible route between the bottom plate and top plate. The $E_{120}$ mode and the $E_{220}$ mode can be used as higher modes.

The resonant frequency of the profile sensor with a resonator filling (for example ceramic material of dielectric constant=E) can be estimated roughly by using the known expressions applicable to a closed resonator. In the case of a circular cylindrical resonator with a resonator diameter D, it can be said for the $E_{mn0}$ mode that:

$$f = cX_{mn} / (\pi \sqrt{\varepsilon} D)$$

(c=velocity of light in a vacuum, $X_{mn}$=n-th zero term in the m-th order Bessel function).

In the case of a rectangular resonator with the internal edge lengths transverse with respect to the profile direction A and B, it can be said for the $E_{mn0}$ mode that:

$$f = \frac{c}{2\pi\sqrt{\varepsilon}} \sqrt{\left(\frac{\pi}{A}m\right)^2 + \left(\frac{\pi}{B}n\right)^2}$$

The distance between the bottom plate and top plate can thus be made extremely small without significantly changing the resonant frequency of the sensor. However, this distance is the governing factor for the three-dimensional focusing of the measurement field. The distance between the top and bottom is thus limited primarily by the length required for the injection antennas. A further limit results from the minimum field strength level required for a successful measurement in the sample area: the smaller the distance is between the bottom plate and top plate in the resonator, the weaker is the field strength in the sample area. In practice, this allows position resolutions down to 1 mm to be achieved in the longitudinal direction. In the case of cigarette profile measurement, focusing to 3 mm is adequate, while focusing to 2 mm is adequate for wood-fibre board profile measurement.

The resonator cavity is provided by two apertures for the sample to be measured to pass through, although these apertures must be supplemented by 2 (at least 5 mm long in the case of the fundamental mode and at least 10 mm long for higher modes) metallic chimneys above and below the resonator area. It is thus not possible for any microwaves to emerge through the apertures for the top and bottom of the resonator. This is because, as long as the dielectric constant of the sample material to be measured is less than a critical value (which is satisfied for all samples), the cutoff frequency that is typical for propagation in the connecting chimneys is considerably higher than the resonant frequency of the resonator. An approximate measure of the critical DC (dielectric constant, for air-filled circular cylindrical resonators whose third mode number is zero is provided approximately by the square of the ratio of the resonator diameter D and that of the sample tube diameter d, $DC_{crit}=(D/d)^2$, giving a critical DC of 81 if D=90 mm and d=10 mm. The microwave intensity therefore falls very quickly and exponentially in the longitudinal direction, and the measured losses result solely from the characteristics of the product and not from radiated emission effects.

Figure 3:
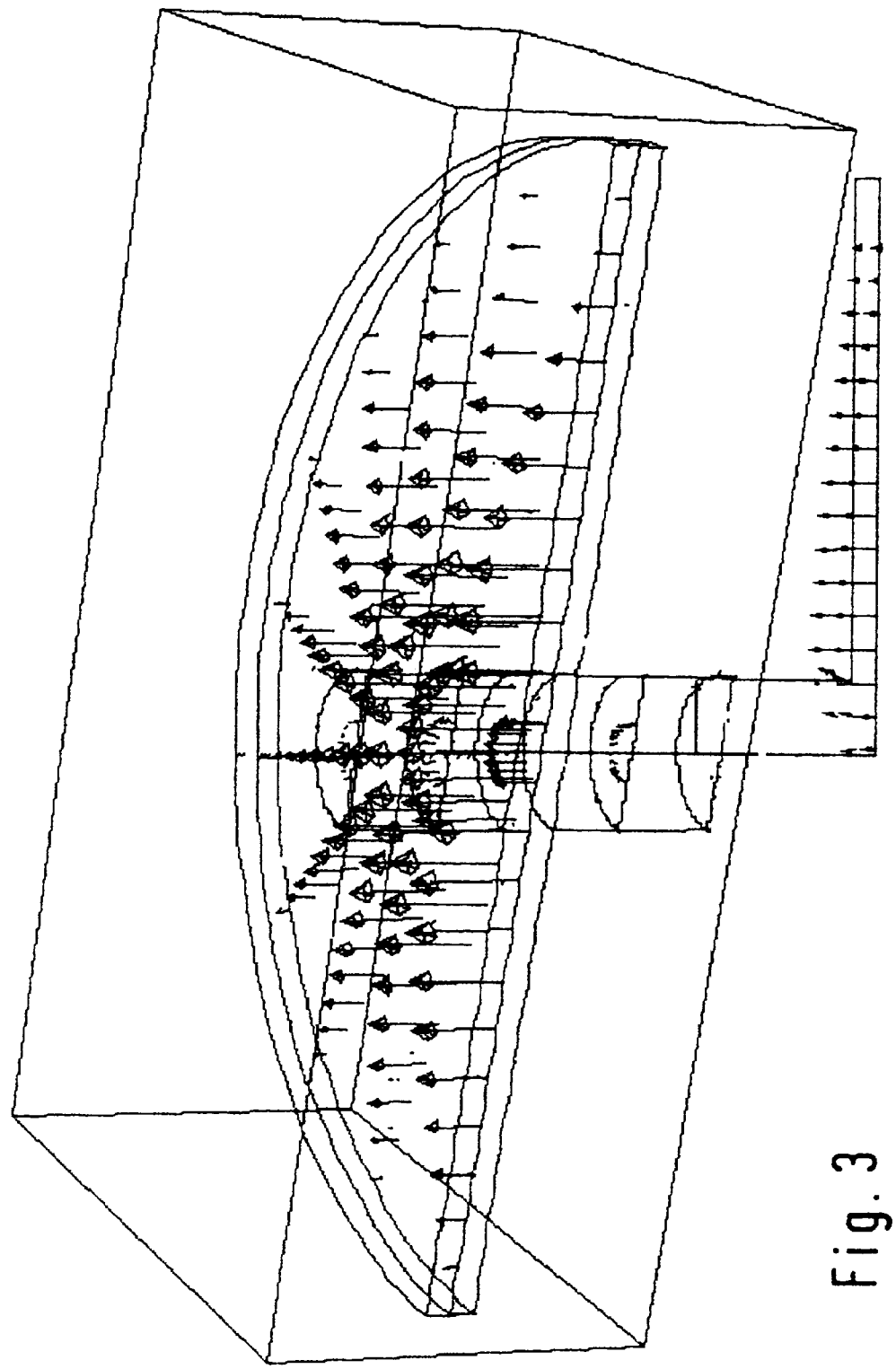
FIG. 3.

FIG. 3 shows the computer simulation of the electrical field distribution in the circular cylindrical profile sensor in the fundamental resonance mode $E_{010}$, the electrical field not being at its maximum in the sample area, as in the case of a closed sensor, but being at a local minimum owing to the two closely adjacent top and bottom surfaces.

The resonant frequency of this exemplary embodiment of a cigarette profile sensor for moisture and density measurement is 2589 MHz for a resonator diameter of 90 mm, a sample tube diameter of 10 mm and a distance of 3 mm between the bottom plate and top plate, if the resonator is not filled with a dielectric.

By filling the resonator body (outside the sample tube) with microwave ceramic material 1, as is illustrated in FIG. 1, this on the one hand allows the geometric form of the sensor to be reduced in size. Using ceramic with a dielectric constant of 9.2 results in the diameter of the resonator body being reduced from 90 mm to 35 mm, if the resonant frequency remains approximately the same. This is necessary for profile measurement with modern cigarette machines since, nowadays, two parallel cigarette production-lines are normally manufactured, running at a distance of 50 mm apart, and the fitting of resonators must not interfere with the double production-line arrangement.

Figure 4:
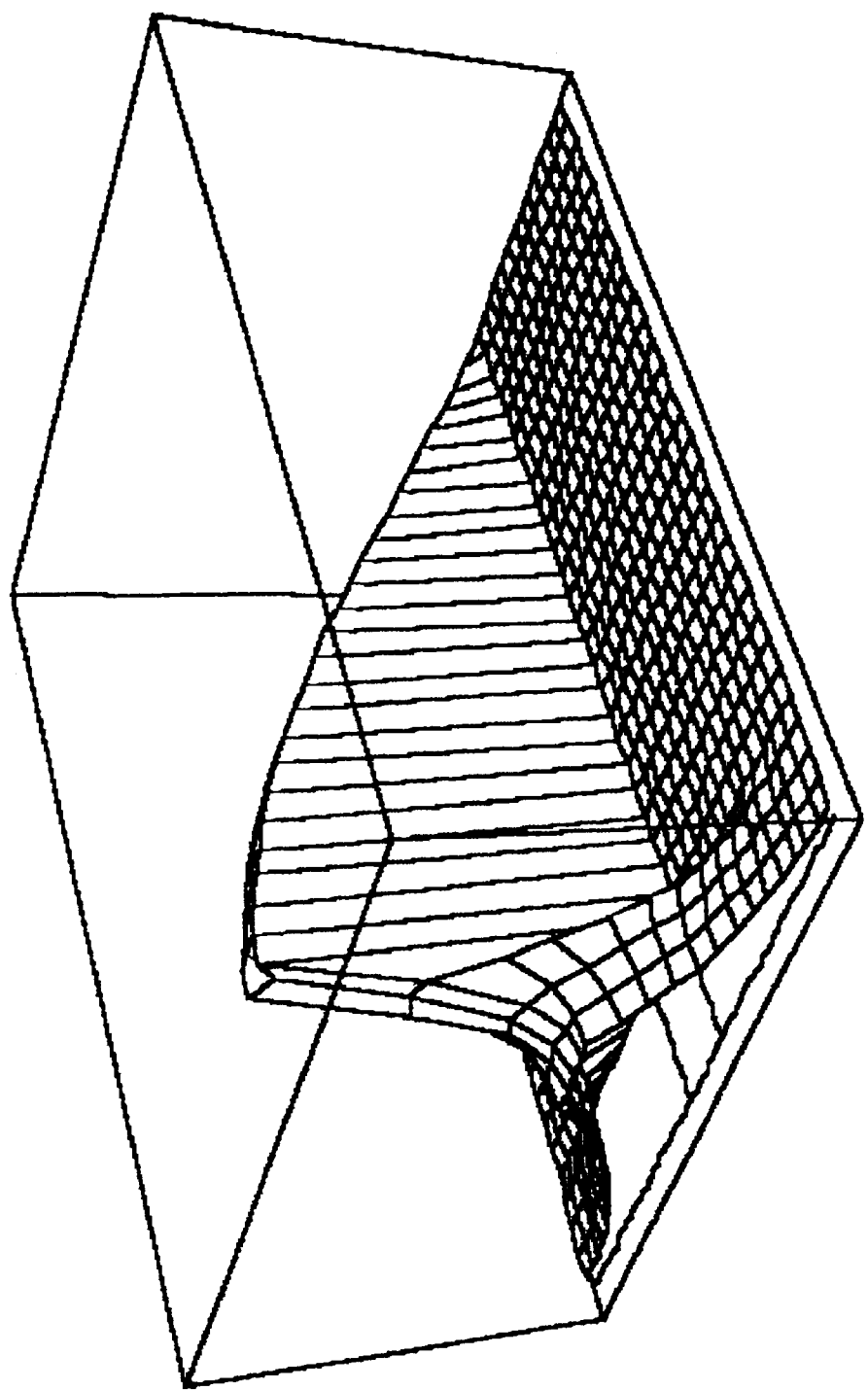
FIG. 4 show the profile of the electrical field lines in a circular cylindrical resonator.

On the other hand, the ceramic insert results in the field being more strongly focused, since without any ceramic, the position resolution in the sample tube is limited by the exponential decay of the electrical measurement field. This "focusing loss", which is counteracted by this ceramic insert, is illustrated in FIG. 4.

Figure 5A:
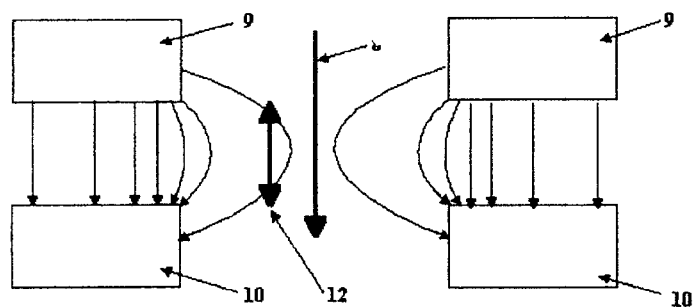
FIG. 5a shows the field line profile in a microwave resonator, in the vicinity of where the sample passes through, without dielectric within the resonator.
Figure 5B:
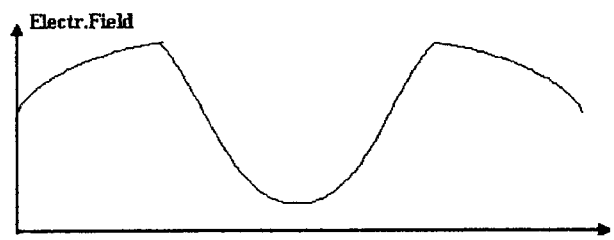
Figure 6A:
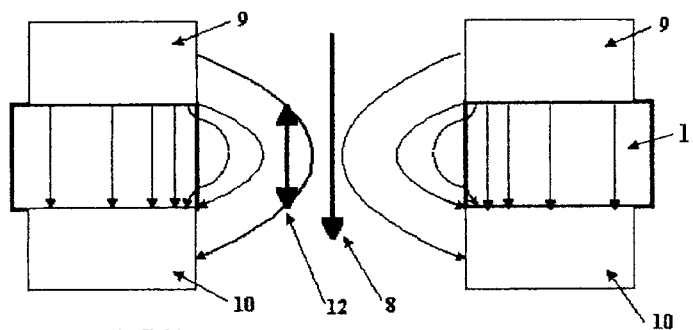
FIG. 6a shows, in a similar view to that in FIG. 5a, the case of a microwave resonator provided with dielectric.
Figure 6B:

FIG. 5a shows the profile of the electrical field lines when there is no dielectric between the metallic walls 9, 10. FIG. 6a shows the corresponding conditions for the situation in which there is a dielectric 1 between the metallic walls 9, 10. In this case, the position resolution is also indicated, by the double arrow 12. The electrical field strength in the lateral direction is shown for both cases in FIGS 5b and 6b. As can be seen immediately, the dielectric ceramic material 1 results in considerably greater homogeneity over the measurement area.

While, in the case of cigarette profile measurement, all types of cigarette that occur in practice can be measured with a sensor in the fundamental mode with a sample opening of 9–10 mm, a special situation arises in the case of profile measurement on chipboards: a sensor is required having a sample tube diameter of up to 35 mm in order to saw a sample from a piece of chipboard, using a suitable tool (for example sawing a circular hole). Since, furthermore, the samples have a considerably higher density, the microwave attenuation resulting from conversion of microwave energy into heat would be too great if the same type of resonator were used as for cigarette profile measurement.

It is therefore advantageous for wooden board profiles to use the higher resonance modes instead of the fundamental mode, such as the $E_{110}$ or $E_{210}$ mode in the case of the circular cylindrical resonator (or the $E_{210}$ or $E_{220}$ modes for a rectangular resonator). The injection method and probe feed are identical to FIG. 1, the only difference being that the dimensions are changed if one wishes to work with about the same resonant frequency (see FIG. 2, which illustrated an exemplary embodiment using the circular cylindrical $E_{110}$ mode with a resonant frequency of 2.5 GHz and resonator internal diameter of 180 mm, sample tube diameter: 35 mm, distance between the bottom plate and top plate: 2 mm, chimney height: 10 mm).

Since the quotient of the resonant frequency spreading and shift in comparison with an empty resonance reference point pair according to the patent cited initially depends only on the moisture but not on the density, this microwave moisture reading can be used for calibration against a direct moisture measurement method (Karl-Fischer-Titration, dry cabinet methods, etc.). At the same time, it is possible to carry out a moisture-independent density calibration by detecting the influence of moisture on the primary microwave density signal, the resonant frequency shift in the density calibration (as a three-dimensional calibration area whose three axes are formed by the axis of the microwave density readings, that of the microwave moisture readings and that of the reference density values).

The special characteristics of these moisture and density calibrations, such as the independence from the specific equipment type, long-term stability, a high level of independence from product type and additives, the independence from the installation region and the surface characteristics (paint, etc.), likewise apply to the sensors envisaged for profile moisture and density measurement.

The most widely different types of cigarette, based on different tobacco mixtures and additives, can be measured and directly compared with one another on this basis, with a single calibration curve both for the density measurement and the moisture measurement. A corresponding situation also applies to the measurement of other samples or elongated materials, such as wood-fibre bore cores, woolen fibers, elongated plastic materials etc.

Figure 7:
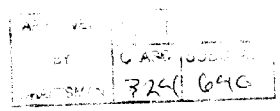
FIG. 7 shows a graphical illustration of the moisture and density profile of a wood-fibre board measured using the instrument as claimed in the invention.
Figure 7:
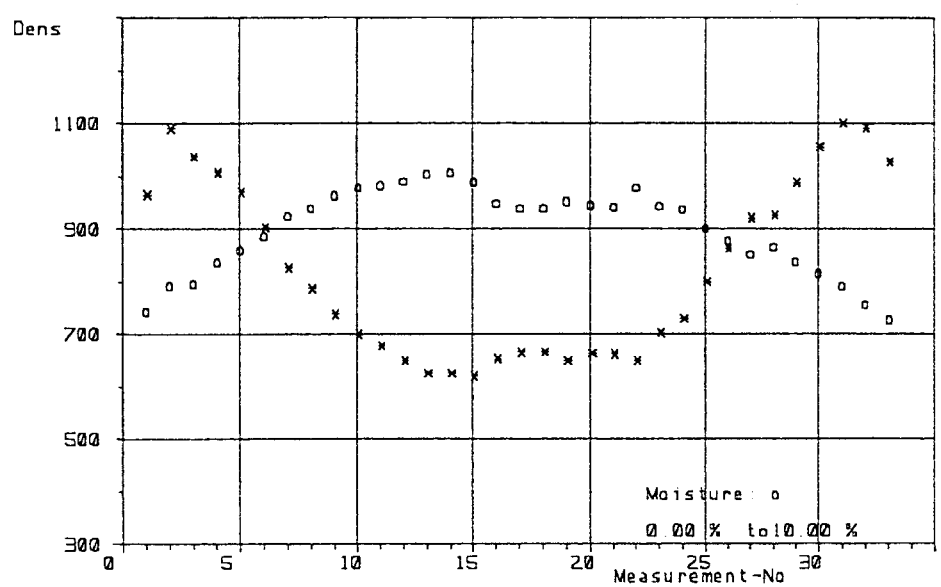
Figure 8:
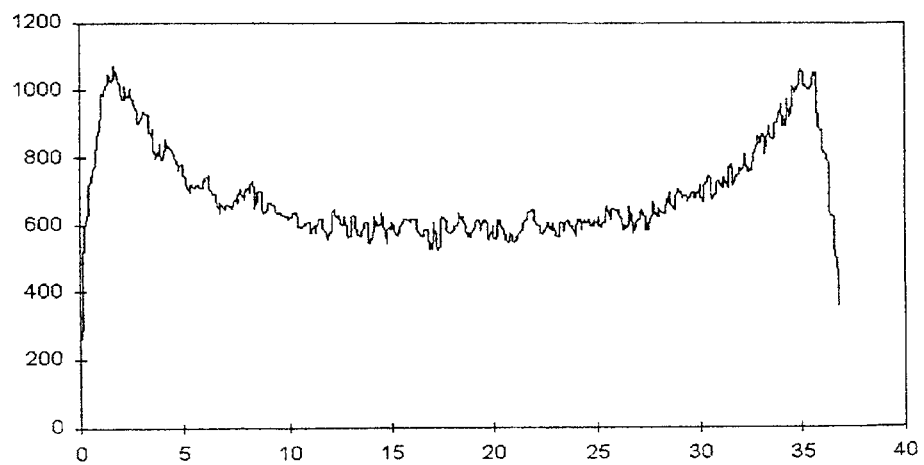
FIG. 8 shows the density profile of the wood-fibre board in FIG. 7, measured with the aid of gamma radiation.

FIG. 7 shows the measurement results obtained with the arrangement in FIG. 2 from simultaneous moisture and density profile measurements in wood-fibre boards. While the moisture levels fall considerably at both sides of the board, as is to be expected, the density levels have a similar profile to the traditional method of gamma radiation profile measurement carried out in parallel. "X" in this case denotes the density in the measurement area 300–1300 $mg/cm^2$, while the moisture is represented by "0" in the range from 0–10%. FIG. 8 shows the corresponding density profile determined from a gamma radiation measurement. The sample thickness in this case was 37 mm, and the sample diameter 35 mm.

Figure 9:
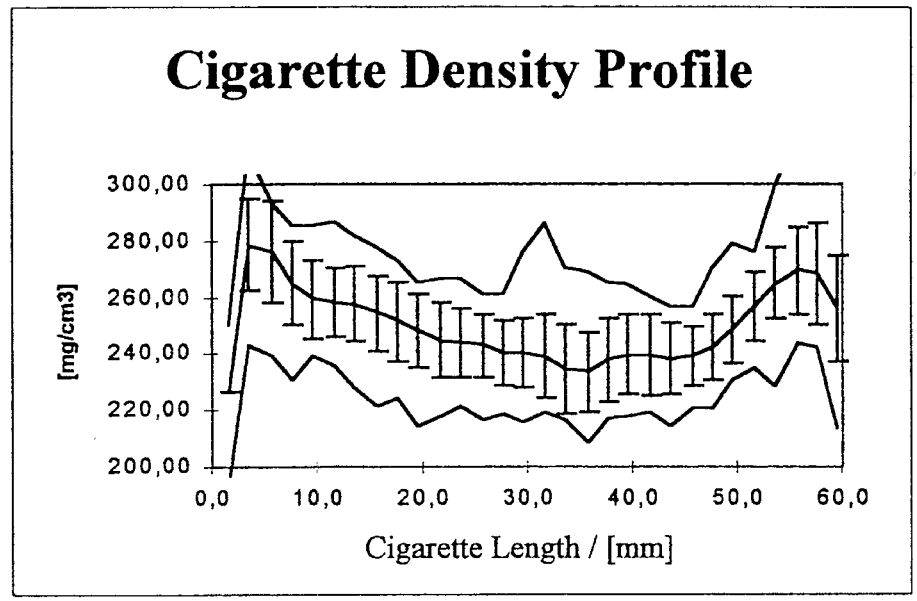
FIG. 9.
Figure 10:
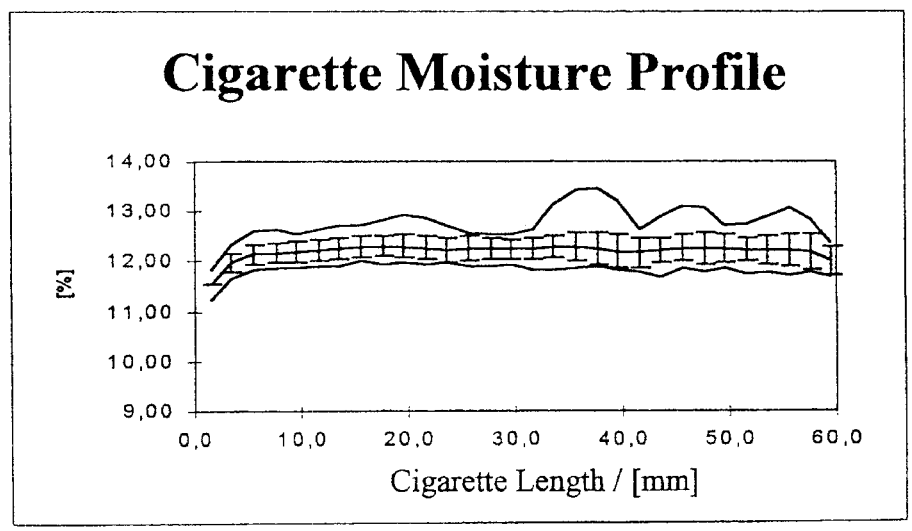
FIG. 10 show the result of the density and moisture profile measurement on cigarettes.
Figure 11:
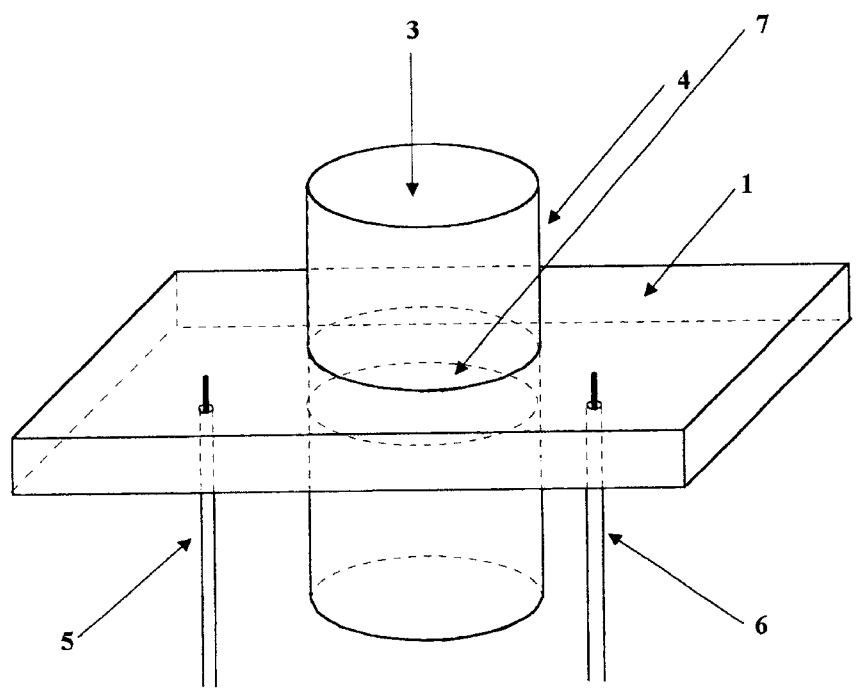
FIG. 11 shows a rectangular microwave resonator according to the invention.

FIGS. 9 and 10 show the results of the simultaneous density and moisture profile measurements on cigarettes. FIG. 11 shows a rectangular microwave resonator.

I claim:

1. A microwave resonator for connection to an instrument for measuring the density and/or moisture profile in the longitudinal direction of a sample comprising a pair of confronting wall members defining therebetween an essentially flat cavity having a thickness considerably less than its lateral extent, a through-hole (3) extending through said wall members and intersecting said cavity at a right angle thereto, said cavity being filled with a dielectric.

2. The microwave resonator as claimed in claim 1, wherein the thickness of the dielectric filled cavity is at least approximately 5 times less than the lateral dimensions.

3. The microwave resonator as claimed in claim 1, characterized in that the thickness of the dielectric filled cavity is at least approximately 10 times less than the lateral dimensions.

4. The microwave resonator as claimed in claim 1, wherein the dielectric has a relative dielectric constant $\epsilon$ of approximately 2 to 100.

5. The microwave resonator as claimed in claim 1, wherein the dielectric has a relative dielectric constant $\epsilon$ of approximately 7 to 15.

6. The microwave resonator as claimed in claim 1, wherein the through-hole (3) is lengthened outward by metallic tubes (4).

7. A microwave resonator as claimed in claim 1, wherein the resonator is cylindrical and is operated in the $E_{n10}$ mode (n=0, 1, 2).

8. A microwave resonator as claimed in claim 1, wherein the resonator is rectangular and is operated in the $E_{110}$, $E_{120}$ or $E_{220}$ mode.

* * * * *